(12) United States Patent
Chen

(10) Patent No.: US 6,452,120 B1
(45) Date of Patent: Sep. 17, 2002

(54) DUAL DIMENSIONAL SHOE SENSOR AND FOOT PEDAL OPERATED SWITCH FOR SURGICAL CONTROL

(75) Inventor: Jerry S. J. Chen, Orange, CA (US)

(73) Assignee: Advanced Medical Optics, Santa Ana, CA (US)

( * ) Notice: Subject to any disclaimer, the term of this patent is extended or adjusted under 35 U.S.C. 154(b) by 0 days.

(21) Appl. No.: 09/569,258

(22) Filed: May 11, 2000

(51) Int. Cl.[7] .................................................. H01H 3/14
(52) U.S. Cl. ............................ 200/52 R; 200/61.58 R; 200/86.5
(58) Field of Search .............................. 210/52 R, 86.5, 210/61.89; 74/512–514; 307/119

(56) References Cited

U.S. PATENT DOCUMENTS

| 4,067,522 A | | 1/1978 | Williams ..................... 246/1 C |
| 4,168,707 A | * | 9/1979 | Douvas et al. .......... 200/86.5 X |
| 4,282,412 A | * | 8/1981 | Florin ....................... 200/52 R |
| 4,837,857 A | | 6/1989 | Scheller ...................... 455/617 |
| 4,933,843 A | | 6/1990 | Scheller et al. ............. 455/617 |
| 4,965,417 A | * | 10/1990 | Massie ...................... 200/86.5 |
| 4,983,901 A | | 1/1991 | Lehmer ...................... 318/685 |
| 5,091,656 A | | 2/1992 | Gahn ......................... 307/119 |
| 5,268,624 A | | 12/1993 | Zanger ....................... 318/551 |
| 5,422,521 A | | 6/1995 | Neer et al. .................. 307/119 |
| 5,423,231 A | * | 6/1995 | Helfrich et al. ......... 200/86.5 X |
| 5,535,642 A | * | 7/1996 | Moll ........................ 74/512 X |
| 5,580,347 A | * | 12/1996 | Reimels ....................... 604/30 |
| 5,643,332 A | | 7/1997 | Stein ............................ 607/49 |
| 5,662,006 A | | 9/1997 | Angeltun .................. 74/594.4 |
| 5,787,760 A | | 8/1998 | Thorlakson .................. 74/512 |
| 5,983,749 A | | 11/1999 | Holtorf ........................ 74/560 |
| 6,050,962 A | | 4/2000 | Kramer et al. .............. 600/595 |
| 6,150,623 A | * | 11/2000 | Chen ......................... 200/86.5 |

FOREIGN PATENT DOCUMENTS

| EP | 0 0 85 518 | 1/1983 |
| FR | 2 646 545 | 4/1989 |
| WO | WO 93/02627 | 2/1993 |
| WO | WO 00/12037 | 3/2000 |
| WO | WO 01/86369 A1 * | 11/2001 |

* cited by examiner

*Primary Examiner*—J. R. Scott
(74) *Attorney, Agent, or Firm*—Walter A. Hackler; Peter Jon Gluck

(57) ABSTRACT

A shoe sensor for surgical control which may be used in combination with a surgical footpedal includes a tilt sensor for determining angular movement and a cuff for supporting the tilt sensor on a user's in position for enabling the tilt sensor to determine lateral angle movement of the user's foot. A connector is provided for transfer of tilt sensor output to a surgical apparatus controller. When used in combination with a footpedal, the shoe sensor enables additional control parameters to be inputed to a controller by using tilt motion of a user's foot.

20 Claims, 5 Drawing Sheets

DUAL DIMENSIONAL SHOE SENSOR AND FOOT PEDAL OPERATED SWITCH FOR SURGICAL CONTROL

The present invention generally relates to apparatus for controlling various apparatus and is more particularly directed to a foot operated control for ophthalmic surgical apparatus such as, for example, for controlling the operation of handpieces during ophthalmic surgery. Still more particularly, the present invention is directed to apparatus for the control of irrigation, aspiration in connection with phacoemulsification of natural lenses.

Ophthalmic surgical apparatus such as phacoemulsification apparatus, hereinabove noted, typically includes operating controls for regulating parameters, or functions, of the apparatus. The apparatus generally includes a handpiece for ultrasonic emulsifying a natural lens while irrigating the eye and aspirating particles of emulsified lens.

Various modalities of operation may be utilized in phacoemulsification apparatus which pertain to controlling various phases of the phacoemulsification procedure.

Typical apparatus includes a control cabinet, power supply, vacuum pump, as well as associated electronic hardware for operating multi-function handpiece in order to sonically emulsify eye tissue, irrigate the eye with saline solution, and aspirate the emulsified lens from the eye.

The control system typically utilizes a footpedal module which enables the operator to control many parameters associated with the operation. Such parameters include the aspiration rate, the intensity power applied to phaco handpiece as well as modes of operation of the handpiece itself. Thus, the use of the handpiece is facilitated by delegating these control functions to the footpedal device.

Heretofore, footpedal device systems have been utilized which provide a variety of pneumatic and electrical actuators to control the ophthalmic surgical apparatus. As an example, the footpedal control systems are described in U.S. Pat. No. 4,983,901 provide for a virtually unlimited number of control variations and modes for operating phacoemulsification apparatus. This patent is incorporated herewith in its entirety in order to provide teaching of the multitude of operating parameters which fall in the scope of the present invention.

Heretofore, footpedals have been limited to detecting angular foot movement, i.e. depression of the footpedal and lateral foot movement, i.e. side switches on the footpedal. This, of course, limits the number of variables controllable by the footpedal.

Because of the importance of the control features provided by footpedals, such devices must be user friendly in order to provide a surgeon the comfort and reliability expected in order not to initiate any disruption of the surgeon's concentration when performing surgery.

As may be expected, different types of footpedals are preferred by various surgeons, with some surgeons preferring an accelerator type pedal in which the sole of the surgeon's foot is utilized for depression, while others desire a pedal operable by the surgeon's toe in order to depress the pedal.

In the past, this has led to the development of a multitude of footpedal devices of diverse configuration in order to provide the comfort and reliability desired by individual surgeons.

Unfortunately, when phacoemulsification apparatus is utilized by a number of physicians, a change in footpedals is often required, which is often inconvenient and may require recalibration of the apparatus. In addition, such alternative footpedals may not be available or offered by a manufacturer.

Accordingly, it is desirable to provide a footpedal which can be utilized by all attending physicians despite their preference for toe or sole activated pedals while at the same time expanding the number of variables controllable by the footpedal. The present invention fulfills that need, while at the same time providing a footpedal which is comfortable to use in either a toe or sole depression configuration.

SUMMARY OF THE INVENTION

The present invention is primarily directed to a shoe sensor for use in surgical control which preferably is used in combination with a footpedal. Accordingly, the invention includes a shoe sensor, footpedal combination.

In accordance with the present invention, the shoe pedal includes a tilt sensor for determining angular movement and a cuff for supporting the tilt sensor on the user's foot in a position for enabling the tilt sensor to determine the lateral angle movement of the user's foot. A connector is provided for transfer of the tilt sensor output to a surgical apparatus controller. The tilt sensor may have an analog or a digital output.

The cuff may include a sleeve for removably attaching the cuff to a user's forefoot and a strap may be provided and attached to the sleeve for extending around the user's heel for preventing forward longitudinal movement of the sleeve on the user's foot. When used in combination with the footpedal, the shoe sensor provides apparatus for providing yet another input to surgical devices, thus providing expanded controllability for a surgical handpiece.

The tilt sensor maybe oriented by the cuff for determining either transverse or longitudinal angular displacement of the user's foot. In one embodiment of the present invention two tilt sensors are provided, one for determining transverse angular movement and another for determining longitudinal angular movement of the user's foot. Accordingly, this provides two additional independent parameters for handpiece control.

A footpedal in accordance with the present invention generally includes a frame having a heel portion and a toe portion with the heel and toe portions being disposed at an angle with one another. A wedge is provided, which has a generally triangular cross section with the first and second sides thereof, subtending a front of the sedge.

A hinge provides a means for pivotally mounting the wedge to the frame which enables the wedge to be flipped between a first position having the wedge first side generally aligned with the frame heel portion and extending therefrom, and a second position having the wedge second side generally aligned with the frame toe portion and extending therefrom.

The structure of the present invention enables the single footpedal to be suitable for physicians desiring an accelerator type, sole contact footpedal, for controlling attached apparatus, and physicians desiring a toe contact footpedal for controlling such apparatus.

More particularly, and importantly, the footpedal may comprise means for enabling the frame heel portion and the wedge first side to assume a flat planar relationship in the wedge first position and for enabling the frame toe portion and the wedge second side to assume a second planar relationship in the wedge second position.

Thus, in either position of the wedge, the foot pedal in accordance with the present invention, allows a comfortable and uniform flat planar area for contacting the sole or toe of a user without discontinuities therein which may prove to be uncomfortable to the user. or interfere with the use of the footpedal.

More particularly, the means for enabling the planar relationship includes mating surface contours in both the frame and the wedge. Still more particularly, the mating surface contours may comprise corrugations in the frame and the wedge.

These corrugations may be aligned with the longitudinal axis of the footpedel, or may be aligned with the transverse axis of the footpedal. In either event, the corresponding corrugations mesh, or nest, with one another when the wedge is either in the first or the second position, which enables alignment of the wedge and frame in one of two planes, depending upon the position of the wedge.

In addition, the footpedal in accordance with the present invention may include a foot activated switch lever, which is disposed adjacent the pedal for enabling activation of the foot activated switch lever by lateral displacement of the user's foot. Two such foot activated switch levers may be provided with one on each side of the pedal for enabling activation thereof by lateral displacement of the user's foot to the right or left, while maintaining contact with the foot pedal itself in either the first or second position of the wedge.

In view of the alternative positions of wedge, switch means may be provided which is disposed in an operative relationship with the wedge for reversing a functional role of the foot activated switch levers in response to the wedge being flipped between the first and second positions.

BRIEF DESCRIPTION OF THE DRAWINGS

The advantages and features of the present invention would be better understood by the following description when considered in conjunction with the accompanying drawings, in which.

DETAILED DESCRIPTION

Figure 1:
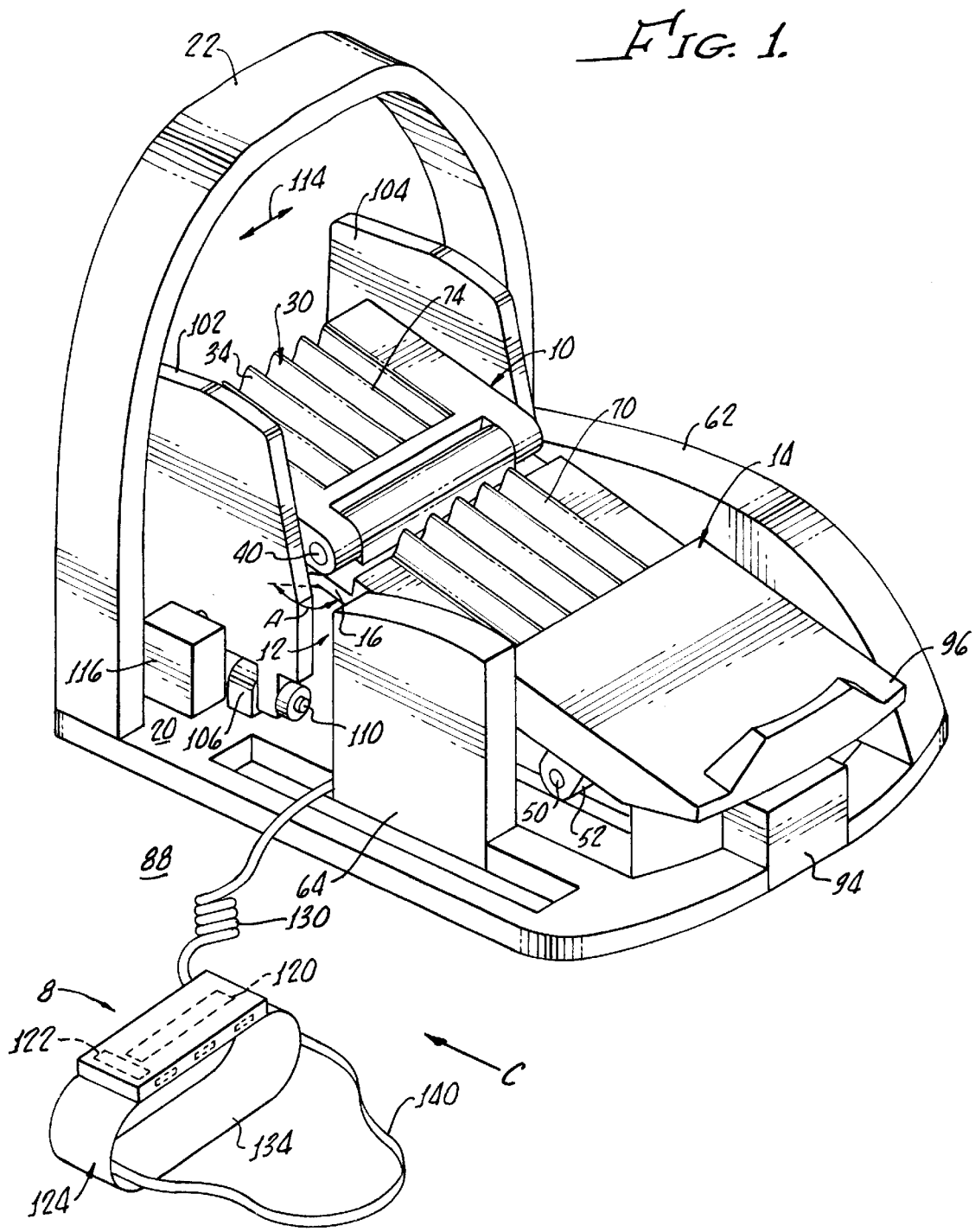
FIG. 1 is a perspective view of apparatus in accordance with the present invention generally showing a shoe sensor and a footpedal with a frame having a heel portion and a toe portion along with a wedge disposed in a first position in which a wedge first side is generally aligned with a frame heel portion.
Figure 2:
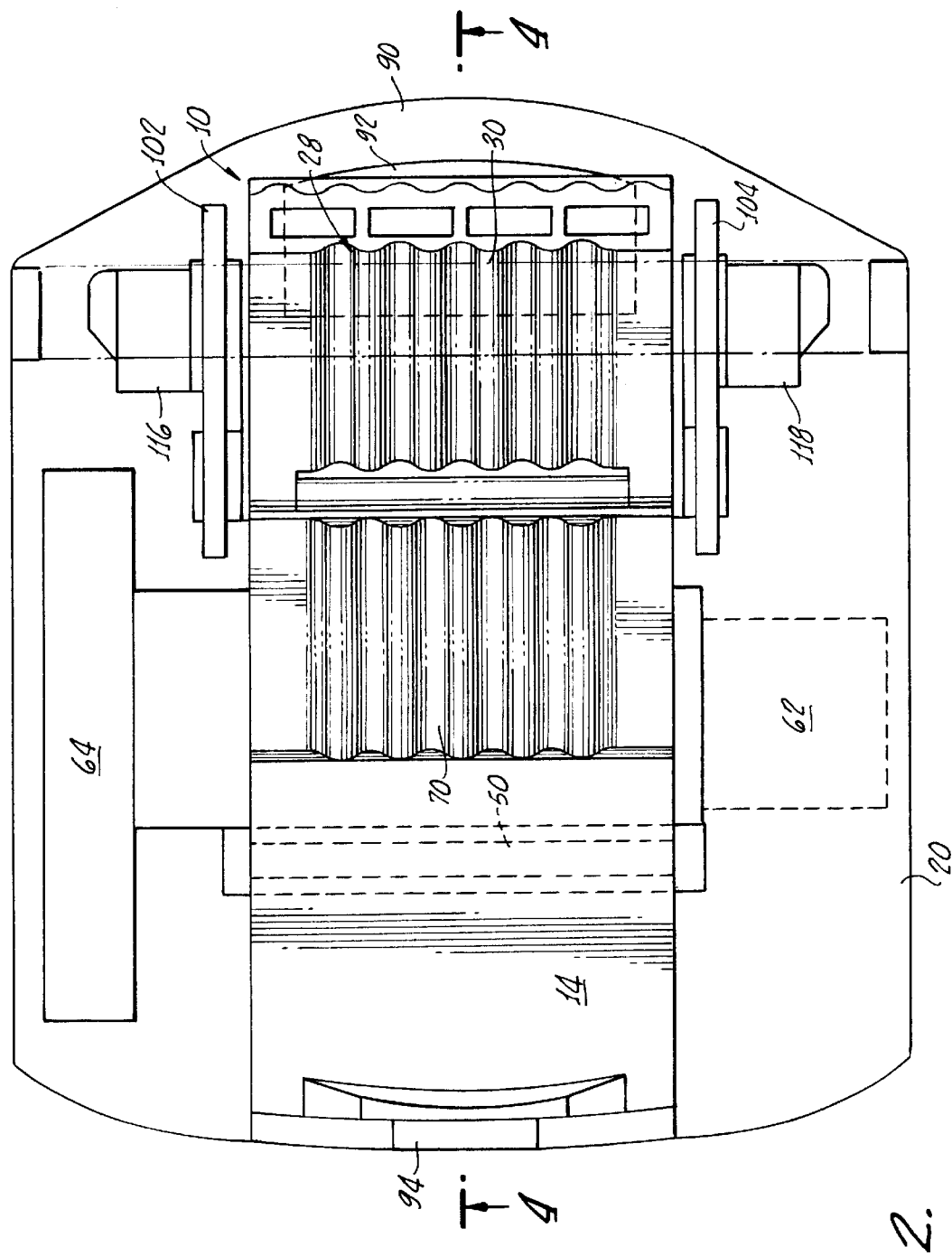
FIG. 2 is a top plane view of the footpedal shown in FIG. 1.

With reference to FIGS. 1 and 2, there is shown apparatus 6 in accordance with the present invention, which includes a shoe sensor 8 and a footpedal 10. The footpedal 10 construction and operation will be described first followed by a description of the shoe sensor 8.

The footpedal generally includes a frame 12 having a heel portion 14 and a toe portion 16, with the heel portion 14 and the toe portion 16, being disposed at an angle A with one another.

Figure 3:
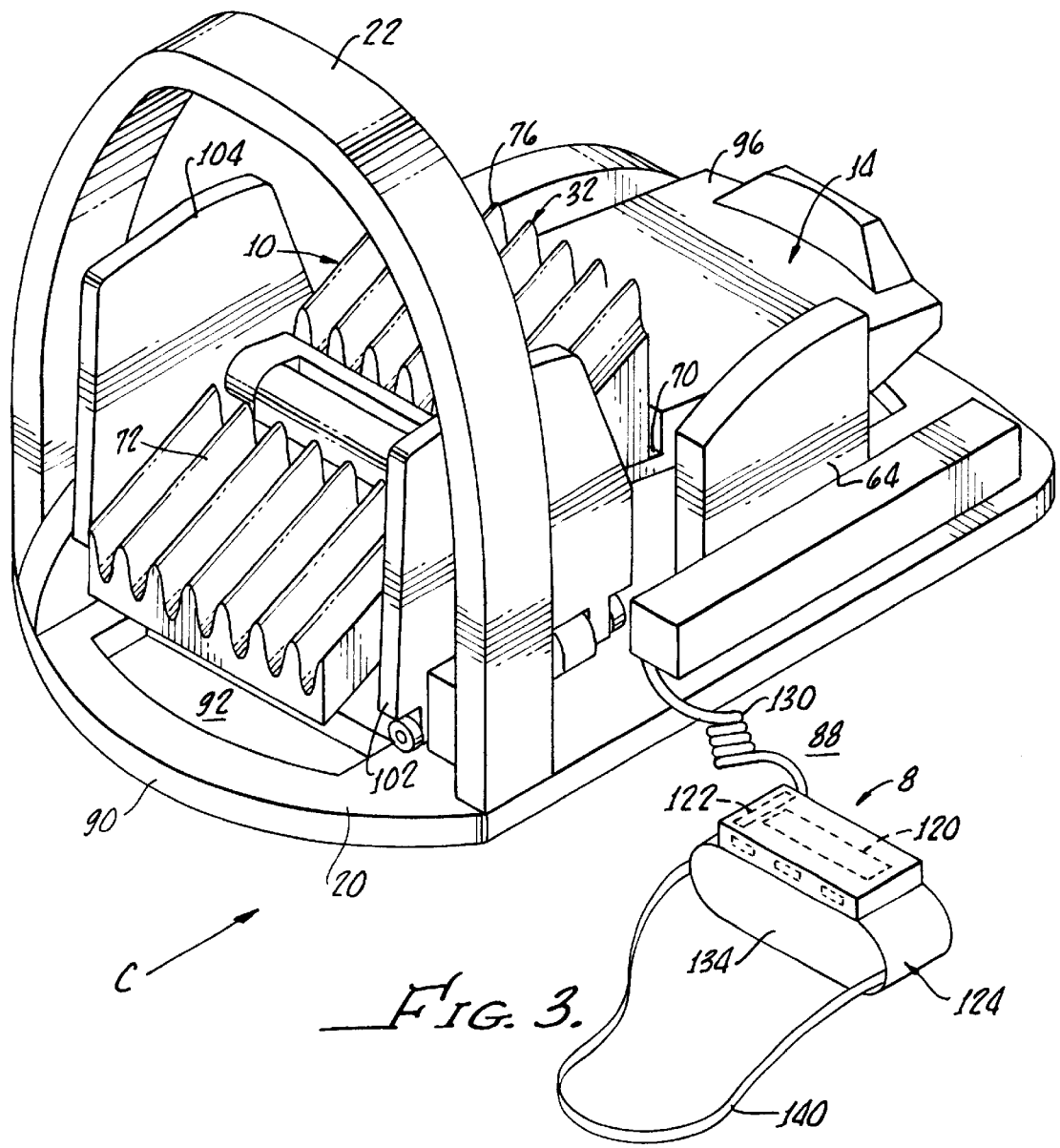
FIG. 3 is a perspective view of the footpedal shown in FIG. 1 with the wedge disposed in a second position and assuming a generally planar relationship with a frame toe portion.

The frame 12 may be formed from any suitable material such as metal or plastic and may be mounted on a base 20 along with a handle 22 for facilitating movement of the footpedal 10 and base as may be necessary to operate the footpedal 10 in either an accelerated type pedal as shown in FIGS. 1 and 2, or in a toe operable configuration as shown in FIG. 3, and hereinafter described in greater detail.

Figure 4:
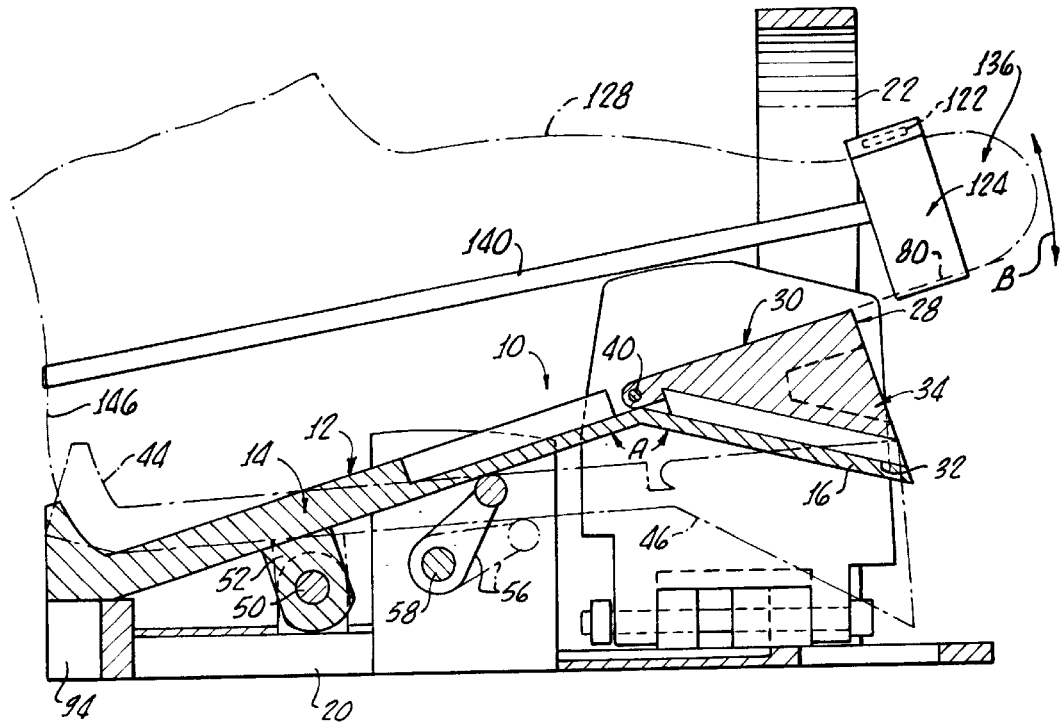
FIG. 4 is a cross sectional view of the footpedal of FIG. 2, showing the wedge in a first position in a flat planar relationship with a frame heel portion and the shoe sensor in position on a user's forefoot in determining longitudinal angular movement of the user's foot.

As also shown in FIG. 4, the footpedal 10 includes a wedge having a generally triangular cross section, with the first side 30 and a second side 32 subtending a front 34 of the wedge 28. The wedge 28 may be formed from any suitable type material such as metal or plastic.

Figure 5:
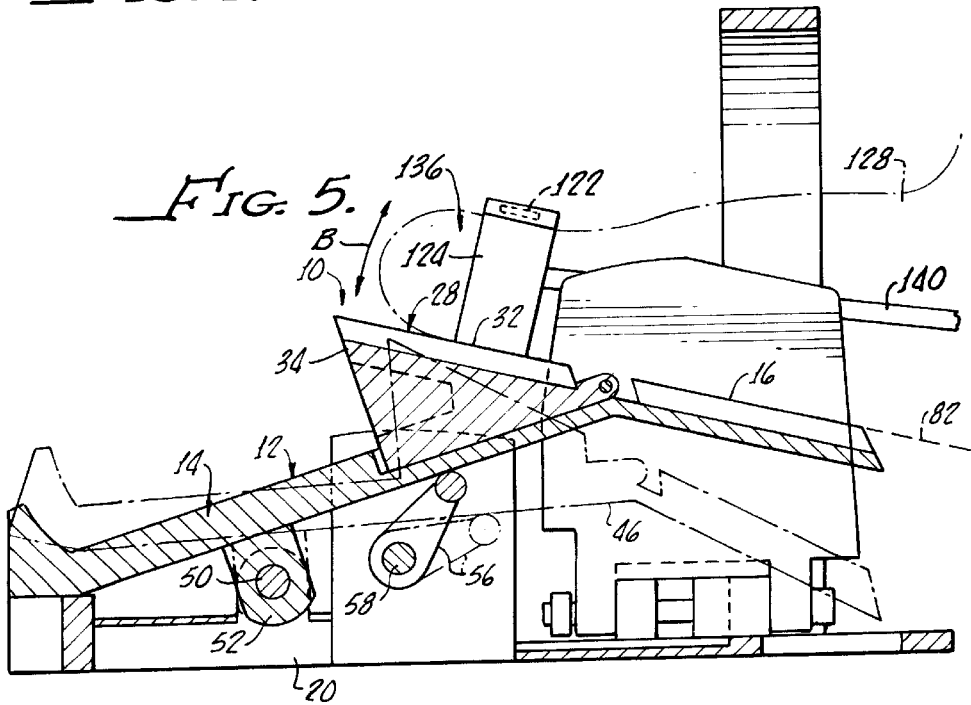
FIG. 5 is a cross sectional view showing the alignment of the wedge and frame to portion when the wedge is disposed in a second position as hereinafter described in greater detail along with the shoe sensor.

A hinge 40 pivotally mounts the wedge 28 to the frame 12 and provides a means for enabling the wedge 28 to be flipped from a first position as shown in FIGS. 1 and 4, and a second position shown in FIGS. 3 and 5.

In the first position, the wedge first side 30 is generally aligned with the frame heel portion 14 and in the second position, the wedge second side 32 is generally aligned with the frame toe portion 16.

As shown more clearly in FIG. 4 in the first position, the footpedal 10 is operable as an accelerator type foot pedal with a depressed position being shown in broken line 44 and FIG. 4.

As shown in FIG. 5, when the wedge 28 is in the second position, the footpedal 10 is operable as a toe depression pedal with a depressed position being shown in broken line 46 in FIG. 5. In either mode of operation, the footpedal 10 is caused to pivot about a pin 50 (see FIGS. 4, 5) mounting the heel portion 14 of the frame 12 to the base 20 by means of a flange 52.

A restoring force to return the footpedal 10 to original positions after depression, as shown in solid line in FIGS. 4 and 5, is provided by a resilient coupling 56 in a conventional manner. Movement of the pedal about a shaft 58 is provided by a conventional shaft encoder 62 (see FIG. 1) which is connected to an onboard computer control assembly 64 for operating remote apparatus such as, for example, a phacoemulsification device (not shown).

Importantly, mating surface contours, namely, corrugations 70 in the frame heel portion 14, see FIG. 1, and corrugated portions 72 in the frame toe portion 16, see FIG. 3, and corresponding corrugations 74 in the wedge first side 30 and corrugations 76 in the wedge second side 32 provide a means for enabling the frame heel portion 14 to assume a flat planar relationship indicated by the dashed line 80 when the wedge 28 is in the first position and for enabling the frame toe portion 16 and wedge second side 32 to assume a second planar relationship, indicated by the dash line 82 (see FIG. 5) when the wedge 28 is in the second position.

This results in an even support for a user's foot (not shown), which may otherwise be interrupted by a protruding hinge (not shown). Such protrusions may cause not only an uncomfortable position for the foot, but may interfere with the action of the foot pedal by the user.

It should be appreciated that, while the corrugations 70, 72, 74, 76 are generally aligned with a longitudinal axis of the foot pedal 10, the corrugations may also be transverse to the longitudinal axis. Furthermore, the mating surfaces, while shown as corrugations, may, in fact, assume any mating surface contour to enable to planar relationships hereinabove described.

Further illustrating the mating relationship between the wedge contours 32 and the frame toe portion corrugations 72 is shown in FIG. 4.

Thus, the footpedal 10 in accordance with the present invention can accommodate users preferring an accelerator type arrangement as shown in FIG. 1 or a toe engagement arrangement as shown in FIG. 3 by merely flipping the wedge 28 from the first position as shown in FIG. 1 to the second position as shown in FIG. 3. To facilitate this flipping a plurality of holes 84 may be provided in a front 34 of the wedge 28 to accommodate a user's finger, or fingers. To reverse the position of the footpedal 10 and base 20 on a floor 88, the handle 22, which also provides a kick guard protection for the footpedal 10, may be used. Alternatively, a second handle, defined by a hole 92 in the base 20., may be utilized for reversing the footpedal 10 position on the floor 88.

A zero switch 94 may be provided and disposed beneath a rear portion of the frame heel portion 14 in order to indicated and provide a signal to the control assembly 64, which is fixed to the frame 20. Electrical interconnections are admitted in the drawings for sake of clarity. The control assembly 64 is configured for cooperating with apparatus (not shown) with which the footpedal 10 is to be used in conjunction therewith.

In that regard, when the footpedal 10 is to be used in conjunction with a phacoemulsification system, for example, foot activated switch levers 102 may be provided. These levers 102 are pivotally attached to the base by brackets 106, 108 and pins 110, 112, which provide means for disposing the foot activated switch levers 102, 104, in a position for lateral displacement, indicated by the arrow 114, of a user's foot (not shown). As a result of such movement, signals to the control assembly 64 are provided by switches 116, 118.

For example, movement of the lever 104 may provide an emergency shut-down of the phacoemulsification equipment with regard to aspiration irrigation fluids, while the lever 102 may be utilized to switch between various modes of operation of the phacoemulsification equipment. All of these functions may be programmed and implemented through the use of the control assembly 64, and/or control equipment associated with the phacoemulsification handpiece. In that regard, a microswitch 118, see FIG. 4, may be disposed in an operative relationship with the wedge 28 for reversing a functional role of the foot activated switch levers 102, 104, in response to the wedge 28 being flipped between the first and second positions.

That is, if an emergency stop situation is to be provided by a right lateral displacement of the foot, as shown in FIG. 4, then the functions of the switch activated levers 102, 104 must be reversed when the wedge 28 is shifted to the second position as shown in FIG. 3.

This is accomplished by utilizing a signal from the microswitch 118 which is interconnected to the control assembly 64 which, when programmed in a conventional manner, can accomplish this objective. Again, interconnecting wires and details with regard to programming are omitted here for the sake of clarity and are obvious to one skilled in the art of programming instrumentation.

Figure 6:
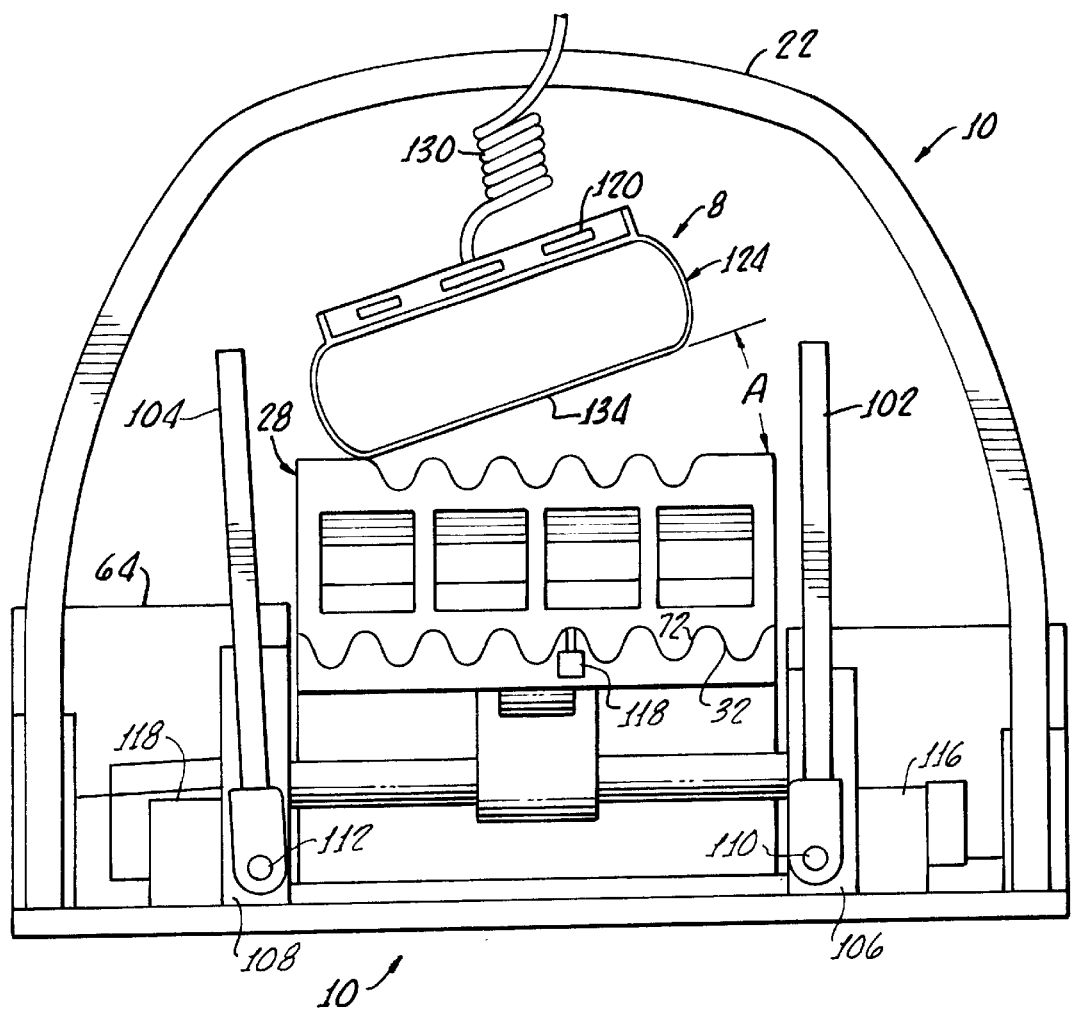
FIG. 6 is a front plane view of the footpedal shown in FIG. 1 showing in greater particularity foot activated levers and the shoe sensor in a tilted, or transverse position.

With reference again to FIGS. 1 and 3–6, the shoe sensor 8 in accordance with the present invention generally includes tilt sensors 120, 122 and a cuff 124 for supporting the tilt sensors 120, 122 on a user's foot 128 shown in broken line in FIGS. 4 and 5. As most clearly shown in FIG. 6, the cuff 124 supports the tilt sensor 120 in a position for enabling the tilt sensor 120 to determine transverse angle, A, movement of the user's foot 128. A connector 130 provides a means for a transfer of tilt sensors 120, 122 output to the controller 64.

The cuff also supports the. tilt sensor 122 in a position for enabling the tilt sensor 122 to determine longitudinal angle, movement of the user's foot 128, as indicated by the double-headed sensor B in FIGS. 4 and 5.

The tilt sensor, 120, 122 may be analog or digital. An analog sensor may provide a linear output as a function of angle. A digital tilt sensor provides an output at a specific lateral angle, for example 10 degrees, and accordingly may function as a switch. A suitable tilt sensor for this purpose is Model No. CW 1300-1 manufactured by T.J. Instruments of Tarzana, Calif.

The cuff may be formed from any suitable material, preferably elastic and include a sleeve 134 which can encircle the user's forefoot 136. In addition, an elastic strap 140 attached to the cuff 124 may be provided for extending around the user's heel 136, see FIG. 4, for preventing forward longitudinal movement of the cuff 124, sleeve 134 and tilt sensor 120 on the user's foot 128.

It should be apparent that the shoe sensor 8 provides for inputting two additional independent parameter for control of surgical apparatus than heretofore available with prior art footpedals.

Although there has been a hereinabove described specific arrangement of a footpedal in accordance with the present invention for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. A shoe sensor for surgical control, the shoe sensor comprising:
   a tilt sensor for determining angular movement, said tilt sensor being selected from a group consisting of an analog output sensor and a digital output sensor;
   a cuff for supporting said tilt sensor on a user's foot in a position for enabling said tilt sensor to determine angular movement of the user's foot; and
   a connector for transfer of tilt sensor output to a surgical apparatus controller.

2. The shoe sensor according to claim 1 wherein said cuff includes a sleeve for removably attaching the cuff to the user's forefoot.

3. The shoe sensor according to claim 2 further comprising a strap, attached to said sleeve, for extending around the user's heel for preventing forward longitudinal movement of said sleeve on the user's foot.

4. The shoe sensor according to claim 1 wherein the tilt sensor is disposed in an orientation for determining transverse angular movement of the user's foot.

5. The shoe sensor according to claim 1 wherein the tilt sensor is disposed in an orientation for determining longitudinal angular movement of the user's foot.

6. The shoe sensor according to claim 4 further comprising a second tilt sensor supported by said cuff in an orientation for determining longitudinal angular movement of the user's foot.

7. In apparatus having a footpedal for operational control of a handpiece during surgery, an improvement comprising:
   a tilt sensor for determining angular movement of a user's foot while the user's forefoot and heel remain in contract with said footpedal, and providing a handpiece control signal corresponding to the angle of the user's foot;

a cuff for supporting said tilt sensor on a user's foot in a position for enabling said tilt sensor to determine lateral angle movement of the user's foot; and a connector for transfer of tilt sensor output to a surgical apparatus controller.

8. The improvement according to claims 7 wherein said cuff includes a sleeve for removably attaching the cuff to the user's forefoot.

9. The improvement according to claim 8 further comprising a strap, attached to said sleeve, for extending around the user's heel for preventing forward longitudinal movement of said sleeve on the user's foot.

10. The improvement according to claim 7 wherein the tilt sensor is disposed in an orientation for determining transverse angular movement of the user's foot.

11. The improvement according to claim 7 wherein the tilt sensor is disposed in an orientation for determining longitudinal angular movement of the user's foot.

12. The improvement according to claim 10 further comprising a second tilt sensor supported by said cuff in an orientation for determining longitudinal angular movement of the user's foot.

13. The shoe sensor according to claims 7, 10 or 13 wherein the tilt sensor is selected from a group consisting of an analog output sensor and a digital output sensor.

14. Apparatus for operation control of a handpiece during surgery, the apparatus comprising:

a foot pedal, said foot pedal comprising:

a frame having a heel portion and a toe portion, the heel and toe portions being disposed at an angle with one another;

a wedge having a generally triangular cross-section with first and second sides subtending a front of said wedge; and hinge means, pivotally mounting said wedge to said frame, for enabling said wedge to be flipped between a first position, having the wedge first side generally aligned with the frame heel portion and extending therefrom to form a first foot platform, and a second position, having the wedge second side generally aligned with the frame toe portion and extending therefrom to form a second foot platform; and a shoe sensor for determining angular movement of a user's foot while the user's forefoot and heel remain in contact with one of the first and second foot platforms, said shoe sensor comprising a tilt sensor for determining the angular movement;

a cuff for supporting said tilt sensor on a user's foot in a position for enabling said tilt sensor to determine lateral angle movement of the user's foot; and a connector for transfer of tilt sensor output to a surgical apparatus controller.

15. The apparatus according to claim 14 wherein said cuff includes a sleeve for removably attaching the cuff to the user's forefoot.

16. The apparatus according to claim 15 further comprising a strap, attached to said sleeve, for extending a round the user's heel for preventing forward longitudinal movement of said sleeve on the user's foot.

17. The shoe sensor according to claim 14 wherein the tilt sensor is disposed in an orientation for determining transverse angular movement for the user's foot.

18. The shoe sensor according to claim 14 wherein the tilt sensor is disposed in an orientation for determining longitudinal angular movement of the user's foot.

19. The shoe sensor according to claim 17 further comprising a second tilt sensor supported by said cuff in an orientation for determining longitudinal angular movement of the user's foot.

20. The shoe sensor according to claims 14, 17 or 18 wherein the tilt sensor is selected from a group consisting of an analog output sensor and a digital output sensor.

\* \* \* \* \*